United States Patent
Whiting et al.

(10) Patent No.: US 7,678,081 B2
(45) Date of Patent: Mar. 16, 2010

(54) METHODS AND DEVICES FOR TRANSSEPTAL ACCESS

(75) Inventors: James S. Whiting, Los Angeles, CA (US); Neal Eigler, Pacific Palisades, CA (US); John L. Wardle, San Clemente, CA (US)

(73) Assignee: Pacesetter, Inc., Sylmar, CA (US)

( * ) Notice: Subject to any disclaimer, the term of this patent is extended or adjusted under 35 U.S.C. 154(b) by 469 days.

(21) Appl. No.: 10/889,319

(22) Filed: Jul. 12, 2004

(65) Prior Publication Data

US 2006/0009737 A1    Jan. 12, 2006

(51) Int. Cl.
*A61M 5/178* (2006.01)
(52) U.S. Cl. .................. 604/164.13; 600/585; 604/135; 604/164.01; 606/108
(58) Field of Classification Search ................ 604/158, 604/159, 163, 164.01–164.09, 164.11, 164.1, 604/164.12, 164.13, 264, 272, 131, 133, 604/135; 606/108, 167–185, 201; 623/1.11; 600/184, 585, 566, 567
See application file for complete search history.

(56) References Cited

U.S. PATENT DOCUMENTS

| | | | |
|---|---|---|---|
| 3,675,651 A * | 7/1972 | Meyer | 604/144 |
| 4,342,313 A | 8/1982 | Chittenden | |
| 4,405,314 A * | 9/1983 | Cope | 604/510 |
| 4,791,937 A | 12/1988 | Wang | |
| 4,969,890 A * | 11/1990 | Sugita et al. | 606/192 |
| 4,986,814 A | 1/1991 | Burney et al. | |
| 4,998,977 A | 3/1991 | Preiss et al. | |
| 5,115,814 A * | 5/1992 | Griffith et al. | 600/463 |
| 5,176,642 A * | 1/1993 | Clement | 604/135 |

(Continued)

FOREIGN PATENT DOCUMENTS

WO    WO 03/077733    9/2003

OTHER PUBLICATIONS

U.S. Appl. No. 11/828,876, filed Jul. 26, 2007, Eigler, et al.

(Continued)

*Primary Examiner*—Anhtuan T Nguyen
*Assistant Examiner*—Kathleen Sonnett
(74) *Attorney, Agent, or Firm*—Grant Anderson LLP

(57) ABSTRACT

Systems and methods for penetrating a tissue membrane to gain access to a target site are disclosed. In some examples, systems and methods for accessing the left atrium from the right atrium of a patient's heart are carried out by puncturing the intra-atrial septal wall. One embodiment provides a system for transseptal cardiac access that includes a guiding catheter, an access catheter and a guidewire. The access catheter may include a tissue penetration member disposed within a housing wherein the tissue penetration member is substantially contained within the housing when in a retracted configuration. When the distal end of the access catheter is disposed adjacent the septal wall, the user can initiate an actuator switch, which may be in a proximal portion of the system, to cause the tissue penetration member to extend through the septal wall. Alternatively, the tissue penetration member can be actuated automatically by a contact trigger mechanism, without initiation by the user, upon contact with the septal wall by a distal contact member which is coupled to the contact trigger mechanism. Such a system may also include an interlock mechanism to prevent triggering of the tissue penetration member at undesirable times during a procedure.

14 Claims, 13 Drawing Sheets

U.S. PATENT DOCUMENTS

| | | | |
|---|---|---|---|
| 5,190,528 A | | 3/1993 | Fonger et al. |
| 5,250,038 A | * | 10/1993 | Melker et al. ............... 604/264 |
| 5,312,341 A | | 5/1994 | Turi |
| 5,324,304 A | | 6/1994 | Rasmussen |
| 5,396,902 A | | 3/1995 | Brennan et al. |
| 5,409,469 A | | 4/1995 | Schaerf |
| 5,415,639 A | | 5/1995 | VandenEinde et al. |
| 5,427,119 A | | 6/1995 | Swartz et al. |
| 5,488,960 A | | 2/1996 | Toner |
| 5,497,774 A | | 3/1996 | Swartz et al. |
| 5,617,854 A | | 4/1997 | Munsif |
| 5,628,316 A | | 5/1997 | Swartz et al. |
| 5,640,955 A | | 6/1997 | Ockuly et al. |
| 5,662,119 A | | 9/1997 | Brennan et al. |
| 5,713,867 A | | 2/1998 | Morris |
| 5,715,818 A | | 2/1998 | Swartz et al. |
| 5,725,512 A | | 3/1998 | Swartz et al. |
| 5,800,413 A | | 9/1998 | Swartz et al. |
| 5,807,306 A | | 9/1998 | Shapland et al. |
| 5,807,326 A | | 9/1998 | O'Neill et al. |
| 5,807,395 A | | 9/1998 | Mulier et al. |
| 5,810,730 A | | 9/1998 | Swartz et al. |
| 5,814,027 A | | 9/1998 | Hasset et al. |
| 5,814,028 A | | 9/1998 | Swartz et al. |
| 5,830,222 A | | 11/1998 | Makower |
| 5,840,027 A | | 11/1998 | Swartz et al. |
| 5,861,003 A | | 1/1999 | Latson et al. |
| 5,871,531 A | | 2/1999 | Struble |
| 5,873,842 A | | 2/1999 | Brennan et al. |
| 5,879,296 A | | 3/1999 | Ockuly et al. |
| 5,902,289 A | | 5/1999 | Swartz et al. |
| 5,902,329 A | | 5/1999 | Hoffman et al. |
| 5,902,331 A | | 5/1999 | Bonner et al. |
| 5,935,160 A | | 8/1999 | Auricchio et al. |
| 5,968,010 A | | 10/1999 | Waxman et al. |
| 5,976,174 A | | 11/1999 | Ruiz |
| 6,004,280 A | | 12/1999 | Buck et al. |
| 6,024,756 A | | 2/2000 | Huebsch et al. |
| 6,068,638 A | | 5/2000 | Makower |
| 6,090,084 A | | 7/2000 | Hasset et al. |
| 6,123,084 A | * | 9/2000 | Jandak et al. ............... 128/898 |
| 6,132,456 A | | 10/2000 | Sommer et al. |
| 6,152,144 A | | 11/2000 | Lesh et al. |
| 6,156,018 A | | 12/2000 | Hasset |
| 6,162,195 A | * | 12/2000 | Igo et al. ............... 604/164.13 |
| 6,190,354 B1 | | 2/2001 | Sell et al. |
| 6,197,001 B1 | * | 3/2001 | Wilson et al. ............... 604/157 |
| 6,200,303 B1 | | 3/2001 | Verrior et al. |
| 6,217,558 B1 | * | 4/2001 | Zadini et al. ............... 604/187 |
| 6,223,087 B1 | | 4/2001 | Williams |
| 6,234,958 B1 | | 5/2001 | Snoke et al. |
| 6,241,728 B1 | | 6/2001 | Gaiser et al. |
| 6,245,054 B1 | | 6/2001 | Fuimaono et al. |
| 6,277,107 B1 | | 8/2001 | Lurie et al. |
| 6,278,897 B1 | | 8/2001 | Rutten et al. |
| 6,280,433 B1 | | 8/2001 | McIvor et al. |
| 6,328,699 B1 | | 12/2001 | Eigler et al. |
| 6,379,346 B1 | | 4/2002 | McIvor et al. |
| 6,402,772 B1 | | 6/2002 | Amplatz et al. |
| 6,408,214 B1 | | 6/2002 | Williams et al. |
| 6,440,120 B1 | | 8/2002 | Maahs |
| 6,456,889 B2 | | 9/2002 | Pianca et al. |
| 6,456,890 B2 | | 9/2002 | Pianca et al. |
| 6,497,698 B1 | | 12/2002 | Fonger et al. |
| 6,526,302 B2 | | 2/2003 | Hasset |
| 6,540,755 B2 | | 4/2003 | Ockuly et al. |
| 6,562,049 B1 | * | 5/2003 | Norlander et al. ............ 606/108 |
| 6,569,182 B1 | | 5/2003 | Balceta et al. |
| 6,579,311 B1 | | 6/2003 | Makower |
| 6,599,288 B2 | * | 7/2003 | Maguire et al. ............... 606/27 |
| 6,602,278 B1 | | 8/2003 | Thompson et al. |
| 6,623,449 B2 | | 9/2003 | Paskar |
| 6,650,923 B1 | | 11/2003 | Lesh et al. |
| 6,656,166 B2 | | 12/2003 | Lurie et al. |
| 6,676,650 B1 | | 1/2004 | Magovern et al. |
| 6,697,677 B2 | | 2/2004 | Dahl et al. |
| 6,733,500 B2 | | 5/2004 | Kelley et al. |
| 6,755,812 B2 | | 6/2004 | Peterson et al. |
| 6,869,414 B2 | | 3/2005 | Simpson et al. |
| 6,893,421 B1 | * | 5/2005 | Larson et al. ........... 604/164.01 |
| 2002/0055711 A1 | * | 5/2002 | Lavi et al. ................... 604/110 |
| 2002/0143255 A1 | * | 10/2002 | Webler et al. ............... 600/459 |
| 2002/0169377 A1 | * | 11/2002 | Khairkhahan et al. ....... 600/433 |
| 2003/0032936 A1 | * | 2/2003 | Lederman ................... 604/507 |
| 2003/0236492 A1 | | 12/2003 | Honebrink |
| 2004/0054335 A1 | | 3/2004 | Lesh et al. |
| 2004/0059280 A1 | * | 3/2004 | Makower et al. ............... 604/8 |
| 2004/0059351 A1 | | 3/2004 | Eigler et al. |
| 2004/0092879 A1 | | 5/2004 | Kraus et al. |
| 2004/0147969 A1 | | 7/2004 | Mann et al. |
| 2004/0215185 A1 | | 10/2004 | Truckai et al. |
| 2006/0074398 A1 | | 4/2006 | Whiting et al. |
| 2006/0079769 A1 | | 4/2006 | Whiting et al. |
| 2006/0079787 A1 | | 4/2006 | Whiting et al. |
| 2007/0083168 A1 | | 4/2007 | Whiting et al. |

OTHER PUBLICATIONS

PCT International Search Report (PCT/US05/35256 mailed Apr. 24, 2007).

PCT International Preliminary Report on Patentability and Written Opinion of the International Searching Authority (PCT/US2005/023720 Mailed Aug. 29, 2007).

Office Action mailed on Jul. 21, 2009 for U.S. Appl. No.: 11/203,624 filed: Aug. 11, 2005 published as: U.S. Appl. No. 2006/0079787 A1 on Apr. 13, 2006.

Office Action mailed on Jan. 12, 2009 for U.S. Appl. No.: 11/203,624 filed: Aug. 11, 2005 published as: U.S. Appl. No. 2006/0079787 A1 on Apr. 13, 2006.

Office Action mailed on Jun. 25, 2008 for U.S. Appl. No.: 11/203,624 filed: Aug. 11, 2005 published as: U.S. Appl. No. 2006/0079787 A1 on Apr. 13, 2006.

Office Action mailed on Jun. 23, 2009 for U.S. Appl. No.: 11/239,174 filed: Sep. 28, 2005 published as: U.S. Appl. No. 2006/0079769 A1 on Apr. 13, 2006.

Office Action mailed on Feb. 9, 2009 for U.S. Appl. No.: 11/239,174 filed: Sep. 28, 2005 published as: U.S. Appl. No. 2006/0079769 A1 on Apr. 13, 2006.

Office Action mailed on Jun. 30, 2008 for U.S. Appl. No.: 11/239,174 filed: Sep. 28, 2005 published as: U.S. Appl. No. 2006/0079769 A1 on Apr. 13, 2006.

Office Action mailed on Apr. 16, 2009 for U.S. Appl. No.: 11/394,149 filed: Mar. 29, 2006 published as: U.S. Appl. No. 2007/0083168 A1 on Apr. 12, 2007.

* cited by examiner

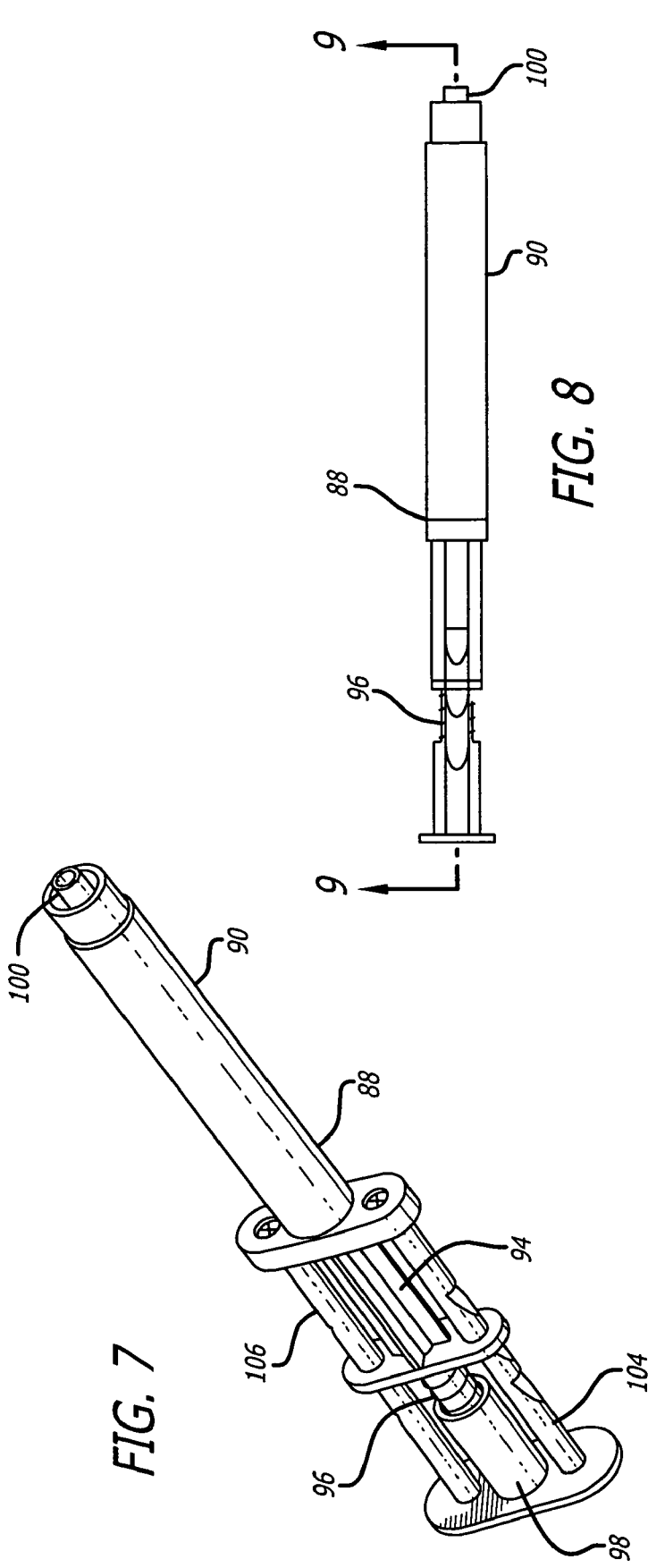

METHODS AND DEVICES FOR TRANSSEPTAL ACCESS

BACKGROUND

Access to the left side of the heart plays an important role in the diagnosis and treatment of cardiovascular disease. Invasive cardiologists commonly perform a left heart catheterization for angiographic evaluation or transcatheter intervention of coronary artery disease. In a left heart catheterization, the operator achieves vascular access through a femoral artery and passes a catheter in a retrograde direction until the catheter tip reaches the coronary artery ostia or crosses the aortic valve and into the left ventricle. From a catheter positioned in the left ventricle, an operator can measure left ventricular systolic and end-diastolic pressures and evaluate aortic valve disease. Ventriculography, where contrast is injected into the left ventricle, may be performed to evaluate left ventricular function. Alternative insertion sites, such as the brachial or radial artery, are used sometimes when femoral artery access is contraindicated due to iliofemoral atherosclerosis, but manipulation of the catheter can be more difficult from these other insertion sites.

Although left heart catheterization can be a fast and relatively safe procedure for access to the coronary arteries and the left ventricle, its usefulness for accessing structures beyond the left ventricle, namely the left atrium and the pulmonary veins, is limited by the tortuous path required to access these structures from the left ventricle via the mitral valve. For example, electrophysiologic procedures requiring access to the left atrium or pulmonary veins, performance of balloon mitral valve commissurotomy, and left ventricular access across an aortic prosthetic disc valve can be difficult, and sometimes unfeasible, through traditional left heart catheterization techniques.

Transseptal cardiac catheterization is another commonly employed percutaneous procedure for gaining access to the left side of the heart from the right side of the heart. Access occurs by transiting across the fibro-muscular tissue of the intra-atrial septum from the right atrium and into the left atrium. From the left atrium, other adjoining structures may also be accessed, including the left atrial appendage, the mitral valve, left ventricle and the pulmonary veins.

Transseptal cardiac catheterization has been performed in tens of thousands of patients around the world, and is used for both diagnostic and therapeutic purposes. Diagnostically, operators utilize transseptal catheterization to carry out electrophysiologic procedures requiring access to the pulmonary veins and also to do left heart catheterizations where an aortic disc prosthetic valve prohibits retrograde left heart catheterizations across the valve. Therapeutically, operators employ transseptal cardiac catheterization to perform a host of therapeutic procedures, including balloon dilatation for mitral or aortic valvuloplasty and radiofrequency ablation of arrhythmias originating from the left side of the heart. Transseptal cardiac catheterization is also used to implant newer medical devices, including occlusion devices in the left atrial appendage for stroke prevention and heart monitoring devices for the treatment of cardiovascular disease.

Transseptal cardiac catheterization is generally successful and safe when performed by skilled individuals such as invasive cardiologists, interventional cardiologists, and electrophysiologists with appropriate training and experience. Lack of success may be attributable to anatomic variations, especially with respect to the size, location and orientation of the pertinent cardiovascular structures and imaging-related anatomic landmarks. Another reason for failure may be the relatively fixed dimensions and curvatures of currently available transseptal catheterization equipment. One major risk of existing transseptal catheterization techniques lies in the inadvertent puncture of atrial structures, such as the atrial free wall or the coronary sinus, or entry into the aortic root or pulmonary artery. In some cases, these punctures or perforations can lead to cardiac tamponade. As such, surgical repair of such a cardiac perforation is sometimes required.

One problem with the standard transseptal needle/catheter system is that once an inadvertent puncture has occurred, it may be difficult to realize what structure has been compromised because contrast injection through the needle is limited by the small bore lumen thereof. Thus, visualization of the structure entered may be inadequate and non-diagnostic. Also, the tip of the catheter dilator of existing devices may cross the puncture site which has the effect of further enlarging the puncture hole.

Other than minor refinements in technique and equipment, the basic transseptal catheterization procedure has remained relatively constant for years. Even so, the technique has several recognized limitations that diminish the efficacy and safety of this well-established procedure. Thus, there remains a need for an alternative system that effectively and safely provides access to the left atrium, or other desired site in the body.

SUMMARY

One embodiment of a device is directed to a transseptal access system including an elongate guiding catheter with a proximal end, a distal end and an inner lumen extending from the proximal end to the distal end thereof. An access catheter is disposed within the inner lumen of the guiding catheter and has an elongate catheter body section with a proximal end, a distal end and a distal section. A body section guidewire lumen is disposed along the elongate catheter body section and a tissue penetration member having a guidewire lumen in fluid communication with the body section guidewire lumen is disposed at the distal section of the elongate catheter body section. The tissue penetration member is axially displaceable in a distal direction with respect to the distal section of the elongate catheter body section. A tissue penetration actuator is configured to impart force in a distal direction on the tissue penetration member. A guidewire configured and sized to be slidably disposed within the body section guidewire lumen and the guidewire lumen of the tissue penetration member may be disposed within the body section guidewire lumen, tissue penetration member guidewire lumen, or both.

An embodiment of a method of accessing the left atrium of a patient's heart from the right atrium of the patient's heart includes providing a system for transseptal access. The system for transseptal access has a guiding catheter with an inner lumen extending along a length thereof and an access catheter. The access catheter is disposed within the inner lumen of the guiding catheter and has an elongate catheter body section with a proximal end, a distal end and a distal section, a body section guidewire lumen disposed along the elongate catheter body section and a tissue penetration member. The tissue penetration member has a guidewire lumen in fluid communication with the body section guidewire lumen and is disposed at the distal section of the elongate catheter body section. A tissue penetration actuator is coupled to the tissue penetration member and configured to rapidly advance the tissue penetration member distally upon actuation.

The guiding catheter is positioned with the distal end of the guiding catheter within the right atrium of the patient's heart.

The distal end of the access catheter is advanced through the inner lumen of the guiding catheter until the distal end of the access catheter is positioned adjacent a desired site of the septum of the patient's heart. The tissue penetration actuator is actuated advancing the tissue penetration member distally through the septum. The guidewire is then advanced through the guidewire lumen of the tissue penetration member until a distal end of the guidewire is disposed within the left atrium of the patient's heart.

These and other advantages of embodiments will become more apparent from the following detailed description when taken in conjunction with the accompanying exemplary drawings.

BRIEF DESCRIPTION OF THE DRAWINGS

FIGS. 7-9 illustrate an embodiment of a pressurized fluid tissue penetration actuator.

DETAILED DESCRIPTION

Embodiments are directed to systems and methods for accessing a second side of a tissue membrane from a first side of a tissue membrane. In more specific embodiments, devices and methods for accessing the left atrium of a patient's heart from the right atrium of a patient's heart are disclosed. Indications for such access devices and methods can include the placement of cardiac monitoring devices, transponders or leads for measuring intracardiac pressures, temperatures, electrical conduction patterns and voltages and the like. The deployment of cardiac pacemaker leads can also be facilitated with such access devices and methods. Such access can also be useful in order to facilitate the placement of mitral valve prosthetics.

Figure 1:
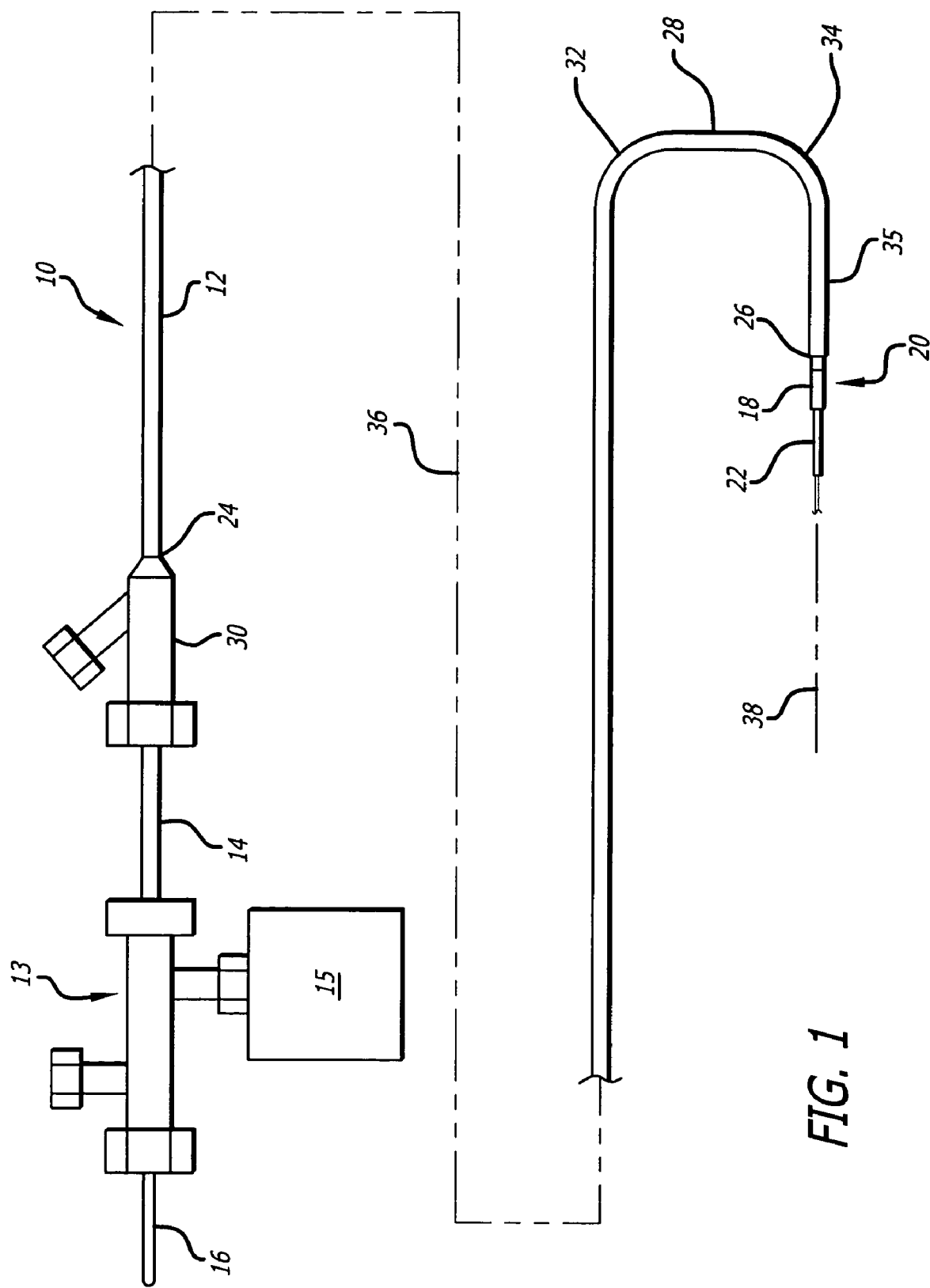
FIG. 1 is an elevational view of a system for transseptal access.
Figure 2:
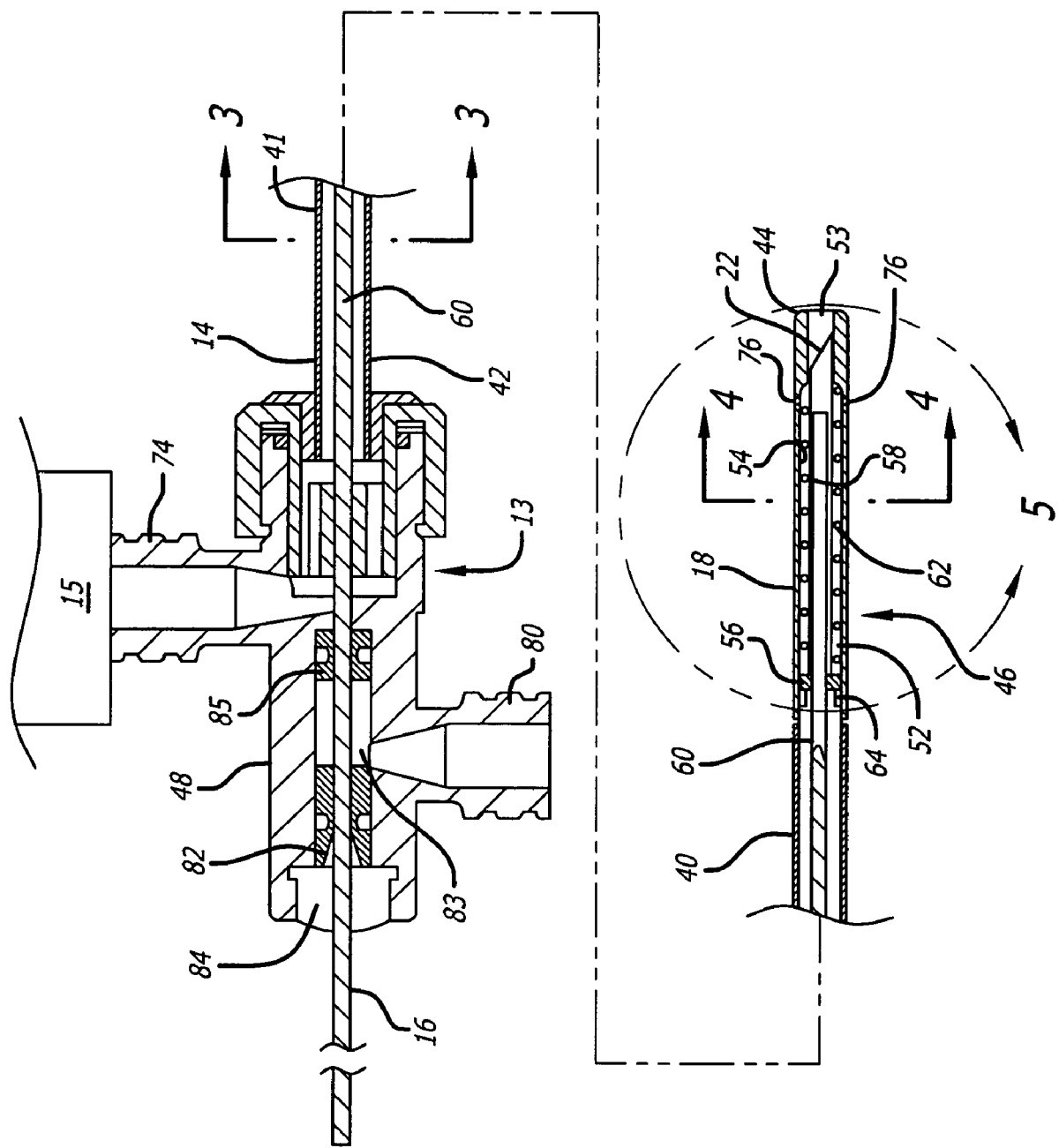
FIG. 2 is an elevational view in partial section and partially cut away of an access catheter of the system for transseptal access of FIG. 1.

FIGS. 1-9 show an embodiment of a transseptal access system 10. Referring to FIG. 1, the transseptal access system includes a guiding catheter 12, an access catheter 14 and a guidewire 16. A housing 18 is disposed at a distal section 20 of the access catheter 14. A tissue penetration member in the form of a hypodermic needle 22 is slidably housed within the housing 18 and is shown in a distally extended or actuated state in FIG. 1. The guidewire 16 is slidably disposed within the access catheter 14. A proximal adapter 13 is disposed at the proximal end of the access catheter 14 and is in fluid communication with a pressurized actuator 15.

The guiding catheter 12 has a proximal end 24, a distal end 26, a distal section 28 and an inner lumen (not shown) extending from the proximal end 24 to the distal end 26. A Y-adapter 30 with a standard Luer type fitting is secured to the proximal end 24 of the guiding catheter. The Y-adapter also has a hemostatic valve at a proximal end of the Y-adapter that may be tightened and sealed against an outer surface of the access catheter 14 in order to prevent leakage of fluids from around the proximal portion of the access catheter 14. The distal end 26 of the guiding catheter has a rounded atraumatic tip shape that facilitates advancement of the guiding catheter through body passages of a patient, such as arteries, veins, bile ducts and the like. The distal section 28 of the guiding catheter 12 has a first curved section 32 and a second curved section 34. The guiding catheter also has a nominal longitudinal axis 36 and a discharge axis 38. The combined curvatures of the first curved section 32 and the second curved section 34 combine to produce a nominal discharge axis 38 that is about 180 degrees from the direction of the nominal longitudinal axis 36. In one embodiment, a straight section 35 of the guiding catheter 12 that is distal of the second curved section 34 can have a length up to about 1.5 cm in order to allow a substantially orthogonal approach to the intra-atrial septum from the right atrium. Embodiments of the guiding catheter 12 may also have a lubricious coating on the inside surface, outside surface or both and may have an outer diameter or transverse dimension of about 4 French to about 12 French. For some embodiments of the guiding catheter, an overall length of about 50 cm to about 70 cm is useful, for others an overall length of about 30 cm to about 50 cm is useful. For use in a transseptal access procedure wherein a femoral approach is used, a length of about 55 cm to about 65 cm is useful. For use in a transseptal access procedure wherein a superior approach is used, a length of about 35 cm to about 45 cm is useful. For some embodiments, an overall length for the guiding catheter 12 can be up to about 110 cm.

Although the distal section 28 of the guiding catheter 12 lies substantially in a single plane, other configurations that have a more three dimensional configuration at the distal section may also be used for this transseptal access system 10, as well as any of the other systems or access catheters discussed herein. For example, depending on the initial access point for a procedure on a patient, guiding catheter designs such as an Amplatz, hockey stick, Judkins, multipurpose configurations and the like may be useful as guiding catheters 12. Examples of suitable access points for transseptal procedures can include inferior routes through the right and left femoral veins and superior routes through the right and left jugular veins and the right and left subclavian veins of a patient. Guiding catheter 12 may also optionally include other features such as radiopaque markers at or near the distal end 26, radiopaque doping of the polymer materials of the guiding catheter and side holes in the distal section 28 in order to facilitate perfusion capabilities. Generally, it is desirable for the guiding catheter 12 to have a configuration, and particularly, a distal section configuration that allows for a substantially orthogonal approach to the membrane or septum across which access is to be gained when the guiding catheter is in position adjacent the membrane or septum.

FIGS. 2-6 illustrate an embodiment of the access catheter 14 of the transseptal access system 10. The access catheter has an elongate catheter body section 40 with a proximal end 42, a distal end 44 and a distal section 46. Proximal adapter 13 is secured to the proximal end 42 of the body section 40. The distal section 46 of the body section includes the housing 18 that surrounds a cylindrical translation chamber 52 that has an inner surface 54. The needle 22, which may include a hypodermic needle having a sharnened tissue penetrating tip, is disposed within the translation chamber 52 of the housing 18 and can slide in an axial direction within the chamber 52 and particularly within the needle lumen 53 disposed at a distal portion of the housing 18. The needle lumen 53 has an inner transverse dimension smaller than the inner transverse dimension of the translation chamber 52 and is configured to allow axial translation of the needle 22 within the needle lumen 53 while minimizing movement of the needle in radial directions during the translation. Thus, some embodiments of the needle lumen 53 act as a bearing for the needle 22.

Figure 5:
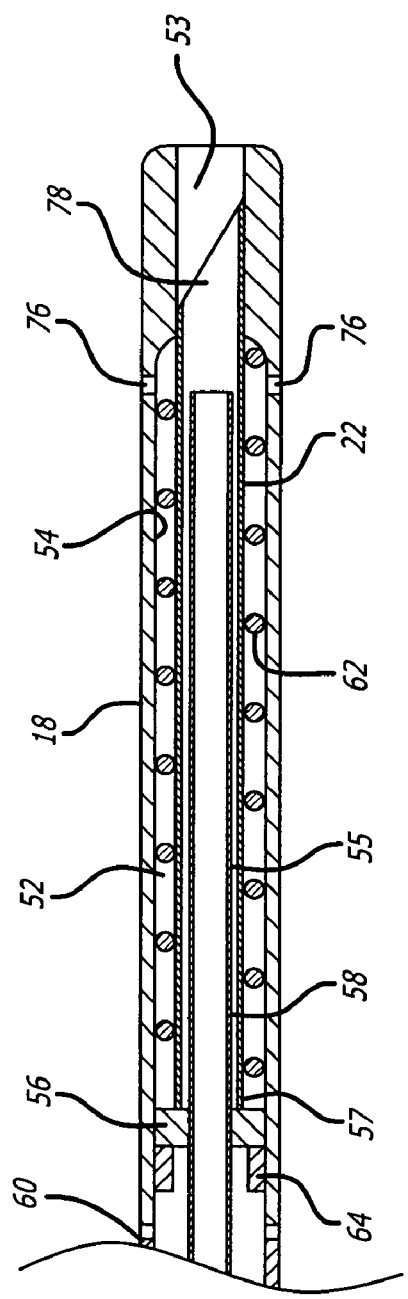
FIG. 5 is an enlarged view of the encircled portion taken along lines 5-5 of FIG. 2 illustrating the tissue penetration member in a retracted state.
Figure 6:
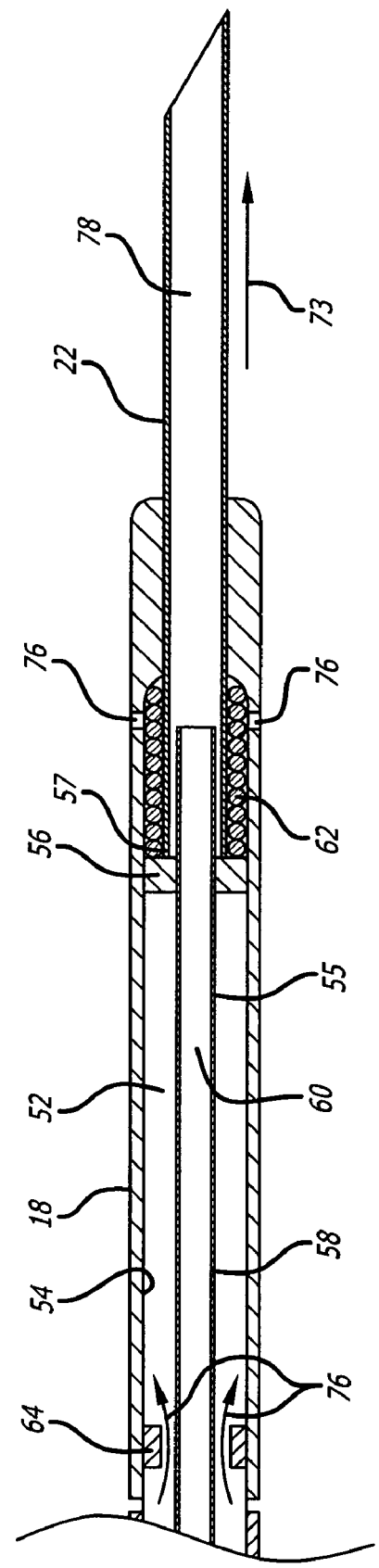
FIG. 6 is an enlarged view of the encircled portion taken along lines 5-5 of FIG. 2 illustrating the tissue penetration member in a distally advanced state after actuation.

Referring to FIGS. 5 and 6, an annular piston 56 is secured to a proximal end 57 of the needle 22 and is sealingly engaged with the inner surface 54 of the translation chamber 52 and an outside surface 55 of a distal section 58 of a tubular element 61 surrounding guidewire lumen 60 within body section 40. The elongate catheter body section 40 may have an outer diameter or transverse dimension of about 0.03 inches to about 0.150 inches and may be made from any suitable medical grade material including polymers such as nylon, polyimide, urethane, PVC and the like. The material used for the outer tubular member 41 of the body section 40 should be flexible enough to navigate tortuous intracorporeal passageways of a patient's body, but maintain sufficient column strength to enable advancement through the guiding catheter 12. Materials having a shore hardness of about 40 D durometer to about 60 D may be useful for the tubular member 41 in some embodiments. Braided reinforcement materials may also be used in the tubular member 41, particularly in embodiments where softer shore hardness materials are used. The access catheter 14 should have a length greater than the guiding catheter to be used with the access catheter 14. In some embodiments, the access catheter has a useable length or length of the body section 40 that is about 2 cm to about 5 cm longer than the guiding catheter 12.

A resilient rebound member in the form of a compressible spring 62 is disposed within the translation chamber 52 between the piston 56 and a distal end of the translation chamber 52. The compressible spring 62 applies a proximally directed force against the piston 56 so as to push the piston 56 against an annular stop 64. The annular stop 64 is secured to the inner surface 54 of the housing 18 and limits the amount of proximal travel of the piston 56 and needle 22 assembly. In the embodiment shown, the spring 62 fills the translation chamber 52 and constantly applies some proximal force on the piston 56, which may serve to retract the needle 22 when the needle is in a relaxed state. This may be useful in order to assure that the needle remains in the retracted position unless actuated for tissue penetration and it may also serve to retract the needle 22 from penetrated tissue once actuation forces are removed. Spring 62 may also be shorter than shown and occupy only a portion of the axial space between the piston 56 and the distal end of the translation chamber when the needle 22 and piston 56 assembly are in the most proximal position. In this configuration, the spring 62 acts as a buffer or rebound spring for the piston and prevents damage to the housing upon actuation and high velocity distal translation of the needle 22. The housing 18 is shown as a substantially cylindrical structure, but may have other suitable configurations. The housing 18 may be made from any suitable material capable of maintaining a substantially rigid structure for consistent axial translation of the piston 56 and needle 22 within the housing 18. The housing may have an outer diameter or transverse dimension of about 0.03 inches to about 0.2 inches and may be made from materials such as stainless steel, Nitinol, MP35N and the like. Suitable composites, such as carbon fiber composites may also be used.

Figure 3:
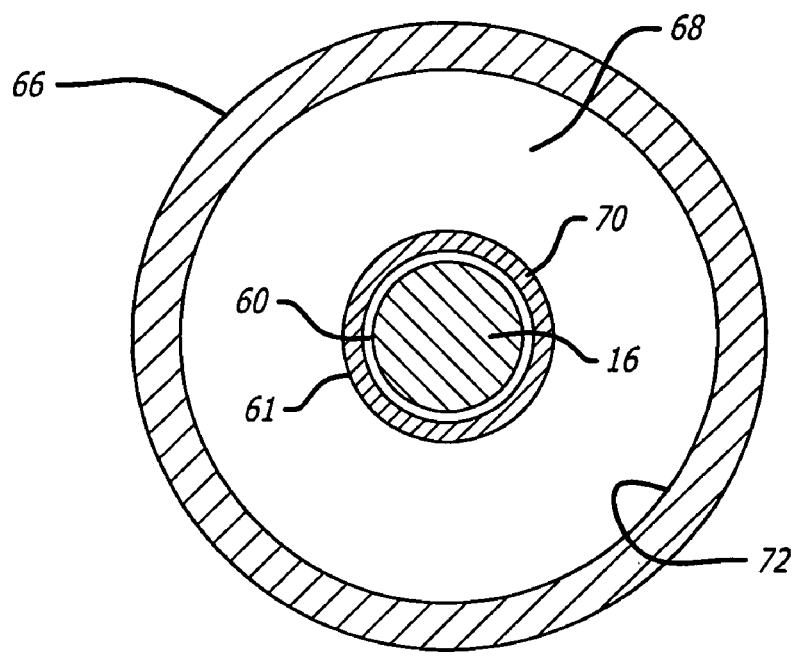
FIG. 3 is a transverse cross section of the access catheter of FIG. 2 taken along lines 3-3 of FIG. 2.
Figure 4:
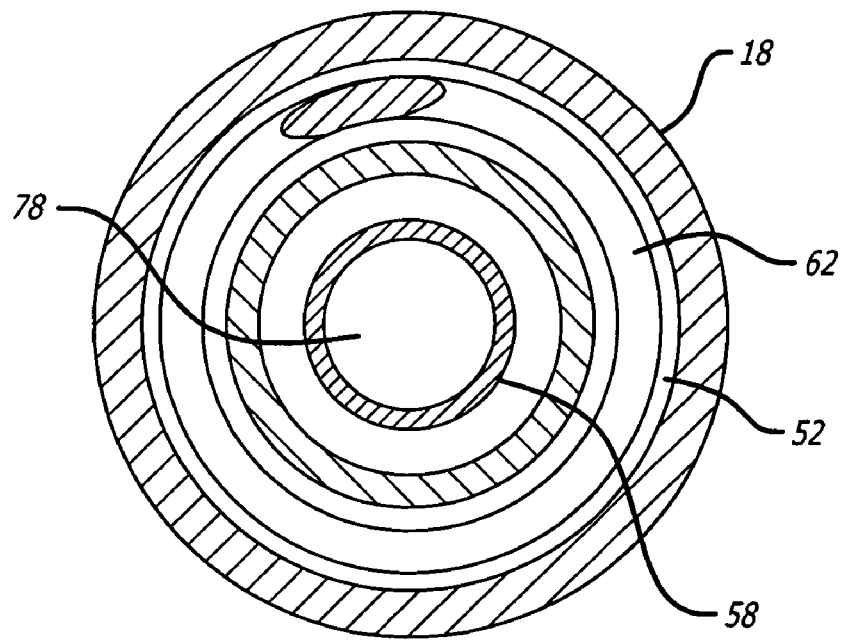
FIG. 4 is a transverse cross section of the access catheter of FIG. 2 taken along lines 4-4 of FIG. 2.

The elongate catheter body section includes an elongate tubular member 66 and the tubular element 61 surrounding the body section guidewire lumen 60, as shown in FIG. 3, with the guidewire 16 slidingly disposed within the body section guidewire lumen 60. An actuation lumen 68 is disposed between an outside surface 70 of the tubular element 61 and an inside surface 72 of the tubular member 66. The actuation lumen acts as a carrier for pressurized fluids, such as suitable gasses and liquids, that emanate or are discharged from the tissue penetration actuator in the form of the pressurized actuator 15 which is secured to Luer port 74 of the proximal adapter 13.

Upon actuation of the pressurized actuator 15, a pressurized fluid is discharged at a high pressure from the pressurized actuator 15 and travels through Luer port 74 of the proximal adapter 13. The pressurized fluid then passes through the port of the proximal adapter 13 and into a proximal end of the actuation lumen 68. The pressurized fluid then travels through the actuation lumen and ultimately into the translation chamber 52 as indicated by arrows 75 in FIG. 6. The actuation of the needle 22 is illustrated in FIGS. 5 and 6 wherein the needle is shown in retracted and extended actuated states, respectively. Upon entering the translation chamber 52, the pressurized fluid impinges against a proximal surface of the piston 56 which is thereby impelled forward in a distal direction at a high velocity, pushing the needle 22 distally in the same manner as indicated by arrow 73. Exhaust ports 76 in the wall of the housing 18 allow fluids distal of the piston 56 to escape the translation chamber 52 as the needle translates distally upon actuation.

For the embodiment shown, when a fluid is discharged from the pressurized actuator 15, and the actuation lumen 68 is filled with the fluid prior to actuation, the fluid actually discharged from the pressurized actuator may never reach the translation chamber 52. It may be, depending on the relative volumes of the actuation lumen 68 and translation chamber 52, that the fluid in the actuation lumen 68 is shifted distally and pressurized from the discharge of the pressurized actuator in order to actuate the needle 22. This is particularly true where the fluid is an incompressible liquid, such as saline solution, and the volume of the actuation lumen 68 is greater than the volume of the translation chamber 52.

In order for the needle 22 to advance distally, the force on the piston 56 produced by the pressurized fluid, as indicated by arrows 75 in FIG. 6, must overcome the retractive proximal force on the piston 56 imparted by spring 62. The needle 22 may remain in the distally extended state shown in FIG. 6 until the force on the piston 56 imparted by the pressure of the pressurized fluid is lowered to the point that the force is overcome by the retractive force of the rebound spring 62. The rebound spring 62 remains in an axially compressed state while the needle 22 and piston 56 are in a distally extended actuated state. As an alternative, if no rebound spring 62 is used, negative pressure or a vacuum from the pressurized actuator 15 may be applied to the translation chamber via the actuation lumen which would then apply a retractive force on piston 56 and needle 22.

Once the needle 22 has been actuated and extended distally through a desired tissue membrane, such as the intra-atrial septum, the guidewire 16 may then be advanced through the body section guidewire lumen 60, into the tissue penetration member guidewire lumen 78, and thereafter exit the distal end of the needle 22. For some procedures, the needle 22 can by a hypodermic needle having a sharpened tissue penetrating tip made from a hollow tubular structure of stainless steel or other suitable medical grade material. For one embodiment, the needle can have a length of about 0.5 cm to about 10 cm, more specifically, about 0.5 cm to about 3.0 cm. The outer diameter or transverse dimension of embodiments of the needle 22 can be from about 0.02 inches to about 0.1 inches, with an inner transverse dimension of the guidewire lumen 78 of about 0.014 inches to about 0.09 inches. Embodiments of the needle may have a wall thickness of about 0.003 inches to about 0.005 inches. The needle 22, piston 56 and housing 18 may be configured in some embodiments to allow distal extension of the needle 22 from the distal end of the housing 18 of about 0.25 cm to about 2.0 cm. In one embodiment, a stainless steel hypodermic needle having a size of about 18 guage to about 22 guage may be used.

As shown in FIGS. 5 and 6, the guidewire lumen 78 of the needle 22 is in fluid communication with the body section guidewire lumen 60. A fluid tight seal between lumens 60 and 78 is maintained by piston 56 which is in sealed contact with the inner surface 54 of the housing 18 and an outside surface 70 of the distal section 58 of the tubular element 61. Elastomeric materials, such as silicone, rubber, soft urethanes and the like may be used for the piston 56 in order to facilitate the sealing function of the piston 56. Referring back to FIG. 2, the proximal end of the body section guidewire lumen 60 is sealed to an inner bore of the proximal adapter 13 and the proximal adapter 13 has a second Luer port 80 which is in fluid communication with a proximal end of the body section guidewire lumen 60. Luer port 80 may be used for flushing the guidewire lumen 60 or injecting diagnostic agents, such as contrast media, through the lumen 60. Luer port 80 may also be used for measuring pressure at the distal end of the access catheter 14, aspirating blood from the distal end, oximetry measurements, and the like.

A proximal sealing gland 82 is disposed within an inner guidewire bore 83 of the proximal adapter 13 and about the guidewire 16 and may be compressed by cap 84 so as to form a seal between the inner guidewire bore 83 of the proximal adapter 13 and an outer surface of the guidewire 16. A distal sealing gland 85 is disposed at a distal end of the inner guidewire bore 83 and against the outer surface 70 of a proximal portion of the tubular element 61. The distal sealing gland 85 may be secured to the outer surface of the proximal portion of the body section guidewire lumen 60, or it may be configured and sized to have an inner sealing lumen therethrough which allows the proximal portion of the tubular element 61 to slide axially within the distal sealing gland 85 while still maintaining a seal. The glands 82 and 85 may prevent leakage of fluids from the body section guidewire lumen 60.

FIGS. 7-9 illustrate an embodiment of a pressurized tissue penetration actuator 88 that may be substituted for the actuator 15 discussed above. The actuator 88 includes a barrel portion 90, a piston 92, a piston shaft 94, an actuator spring 96 and a spring housing 98. A male Luer fitting 100 is disposed at the distal end of the actuator 88 and is in fluid communication with an inner chamber 102 of the actuator 88. The male Luer fitting is configured to be secured to Luer port 74 of the proximal adapter 13 of the access catheter 14 discussed above. A spring housing frame 104 support the spring housing 98 and is coupled to the barrel portion 90 by a ratchet assembly 106. The ratchet assembly 106 allows the actuator spring 96 to be cocked in a compressed state with the piston 92 retracted proximally from a distal end of the barrel portion 90. The ratchet assembly 106 allows the spring to be released upon actuation such that the full compressive force of the spring 96 is applied to the piston shaft 94 and thereby to the piston 92 and the contents of the inner chamber 102 which are then ejected at high pressure from the chamber and into the Luer port 74 of the proximal adapter 13.

Figure 10A:
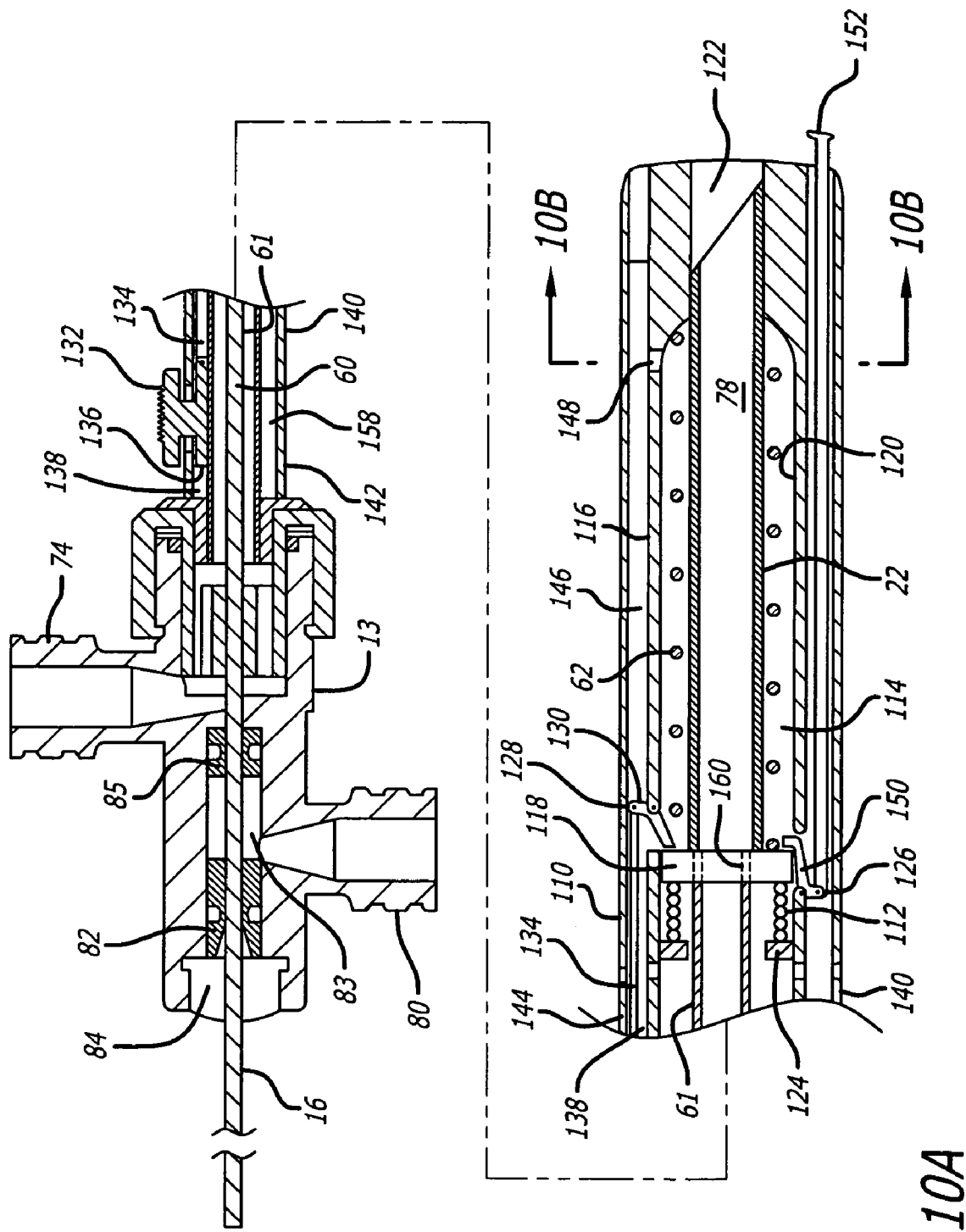
FIG. 10A is an elevational view in longitudinal section of an embodiment of an access catheter having a tissue penetration actuator in the form of a spring and showing the tissue penetration member in a retracted state.
Figure 10B:
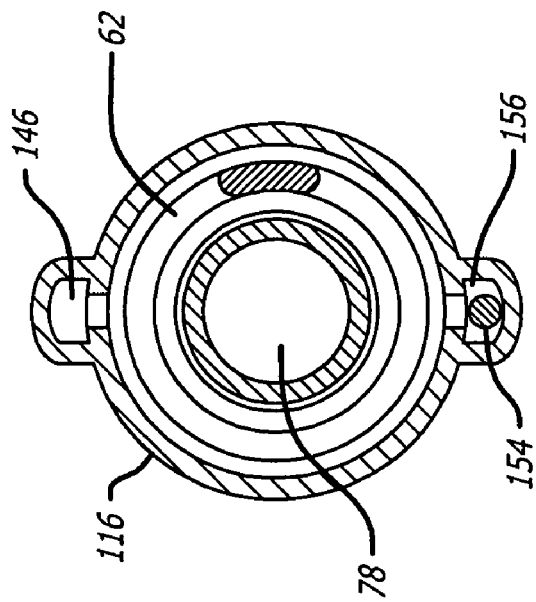
FIG. 10B is a transverse cross section of the access catheter of FIG. 10A taken along lines 10D-10D of FIG. 10A.
Figure 10C:
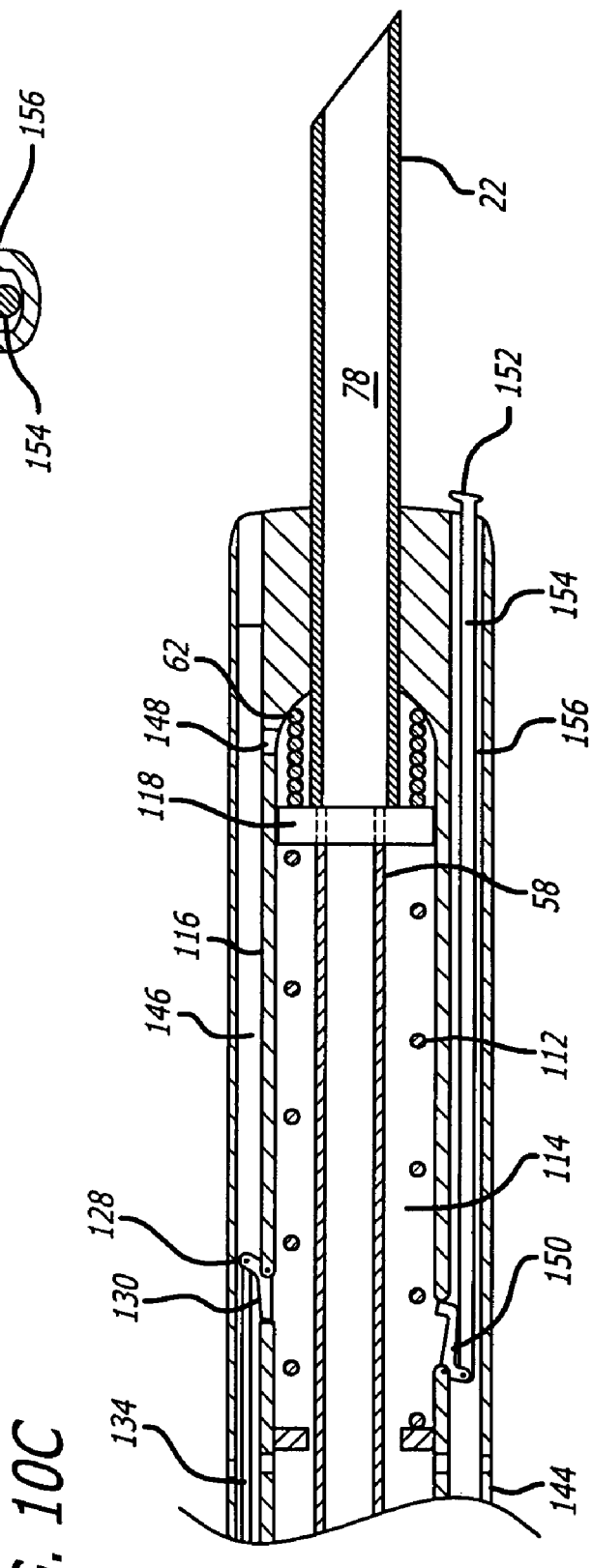
FIG. 10C shows the tissue penetration member of FIG. 10A in a distally advanced state after actuation.

FIGS. 10A-10C illustrate another embodiment of an access catheter 110, which may have uses, features, dimensions and materials which are similar to, or the same as, those uses, features, dimensions and materials of the access catheter 14 discussed above. Access catheter 110 includes a tissue penetration actuator in the form of a spring 112 disposed within the translation chamber 114 of the housing 116. A resilient rebound member spring 62 is disposed in the translation chamber 114 distal of piston 118 which is secured to the distal end of needle 22. Piston 118 need not be sealed against inner surface 120 of the cylindrical translation chamber 114. The needle 22 is slidably disposed within a tissue penetration member lumen 122 of the housing 116.

The spring 112 is axially confined in the translation chamber 114 between the proximal surface of the annular piston 118 and the annular stop 124 which is secured to the inner bore 120 of the housing 116. The spring 112 imposes a distally directed axial force on piston 118. Forward motion of the piston 118 is prevented by a contact trigger mechanism 126 and an interlock mechanism 128. The interlock mechanism 128 has a pivoting catch 130 which mechanically blocks distal motion of the piston 118 when the catch 130 is in the locked position as shown in FIG. 10A. The pivoting catch 130 is operated by a proximal interlock switch 132 which is coupled to the pivoting catch 130 by means of an actuator rod 134. The interlock switch 132 has a barrel 136 that is disposed within an actuator rod lumen 138 which is formed into the elongate body section 140 of the access catheter 110. The proximal end 142 of the elongate body section 140 is secured to the proximal adapter 13 and the distal end 144 of the elongate body section 140 is secured to the proximal end of the housing 116. The actuator rod lumen 138 of the elongate body section 140 has a corresponding lumen 146 on the housing 116. The translation chamber 114 has an optional distal vent 148 that may vent into a distal portion of the lumen 146 in order to vent materials from the translation chamber upon actuation and facilitate high velocity actuation of the needle 22.

The interlock mechanism 128 can be locked by the operator of the access catheter 110 to lock the piston 118 and needle 22 assembly from distal movement and thereby prevent actuation of the needle 22. This may be useful for preventing unwanted actuation of the needle 22 during delivery the access catheter 110 or of a system for trans-membrane access that incorporates the access catheter 110. In addition, if no other restrictions on distal movement or actuation of the needle 22 are in place in the access catheter, the interlock mechanism 128 may be used to manually fire or actuate the needle 22, by manually advancing the interlock switch 132 in a distal direction when the needle 22 is in a retracted or cocked state, with the spring 112 in an axially compressed state. If other locking mechanisms or triggering mechanisms are used, then the interlock mechanism 128 may be used to "arm" the system by advancing the interlock switch 132 in a distal direction once the distal end of the access catheter is properly positioned and it is safe to actuate.

The contact trigger mechanism 126 may be used in a similar fashion to that of the interlock mechanism 128. The contact trigger mechanism 126 also has a pivoting catch 150 which mechanically blocks distal motion of the piston 118 when the catch 150 is in the locked position as shown in FIG. 10A. However, the pivoting catch 150 is actuated by distal contact member 152 which is coupled to the catch 150 by a distal actuator rod 154. The distal actuator rod 154 is disposed within an actuator rod lumen 156 of the housing 116 which may optionally be in communication with a lumen 158 of the elongate body section 140. When a proximally directed force is exerted on the distal contact member 152, the actuator rod 154 pivots the pivoting catch 150 so as to unlock or trigger the contact trigger mechanism 126. The contact trigger mechanism, as the interlock mechanism 128 discussed above, can be used alone, in conjunction with each other, or in conjunction with some other locking or triggering mechanism or mechanisms. Thus, the access catheter 110 could be advanced to a target site with the spring 112 compressed and the needle 22 and piston 118 proximally retracted and cocked, ready to be actuated with both the interlock mechanism 128 and the contact trigger mechanism 126 in the locked position. Thereafter, the system may be actuated two different ways.

In a first method, as a distal end of the access catheter 110 approaches a target site and it is safe for the needle 22 to be actuated, the access catheter 110 can be "armed" by unlocking the interlock mechanism as shown in FIG. 10C. Thereafter, the access catheter is further distally advanced until the distal contact member 152 of the contact trigger mechanism 126 is pressed against tissue adjacent the target site. This forces the distal contact member 152 in a proximal direction and unlocks or triggers the contact trigger mechanism 126 as shown in FIG. 10C, with the needle then be actuated and advanced rapidly in a distal direction as shown. Alternatively, the contact trigger mechanism 126 could be used as a safety interlock assuring contact with tissue prior to actuation of the needle 22. In this second method, the distal end of the access catheter 110 would be advanced to a target tissue membrane with both the interlock mechanism 128 and the contact trigger mechanism 126 in a locked state. The distal end of the access catheter 110 would then be brought into contact with the target tissue, such that the distal contact member 152 unlocks the contact trigger mechanism 126, thereby "arming" the system. The user can then manually actuate the needle 22 by sliding the proximal interlock switch 132.

Upon actuation, spring 112 is allowed to axially expand while pushing the piston 118 and the piston simultaneously compresses the resilient rebound member or spring 62. In this embodiment, the tubular member 61 of the body section guidewire lumen 60 advances distally with the needle 22 as a distal end 160 of the tubular member 61 is secured to the piston 118 with the lumen 60 in fluid communication with the needle guidewire lumen 78. As discussed above, the tubular member 61 of the guidewire lumen 60 can be configured to translate freely in the distal gland 85 while still maintaining a seal. This arrangement of the distal end of the tubular member 61 of the guidewire lumen 60 being secured to the piston 118 may also be used for the embodiment of the access catheter 14 discussed above with the tubular member 61 of the guidewire lumen 60 being secured to the piston 56.

Figure 11A:
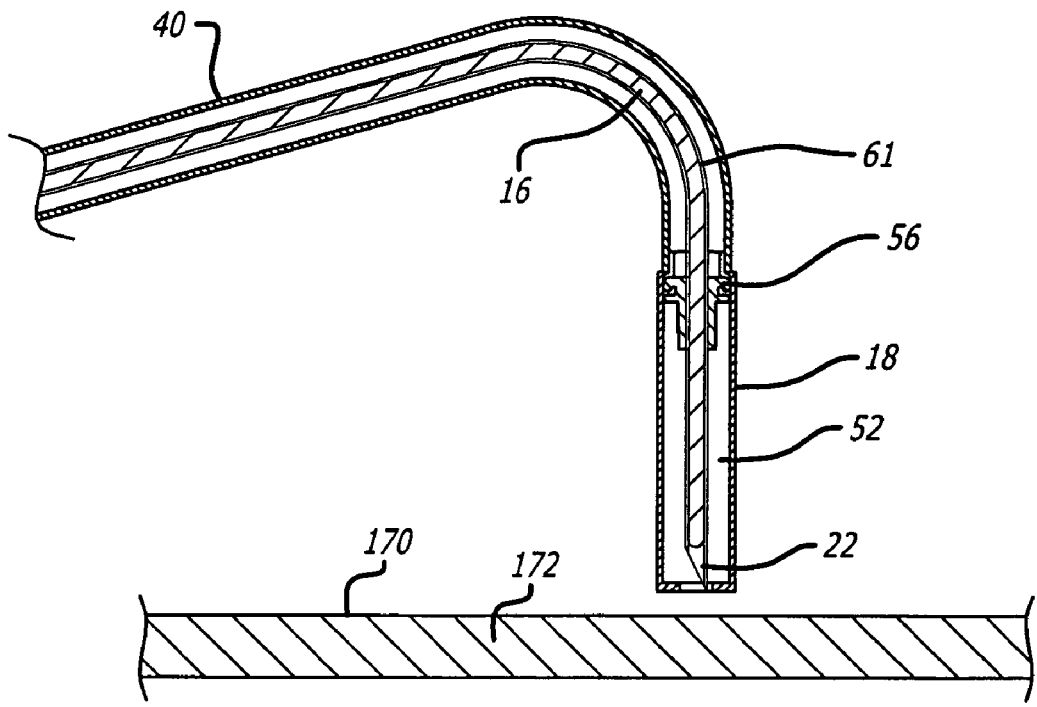
FIGS. 11A-11C illustrate an embodiment of a method sequence of accessing a second side of a tissue membrane from a first side of the tissue membrane.
Figure 11B:
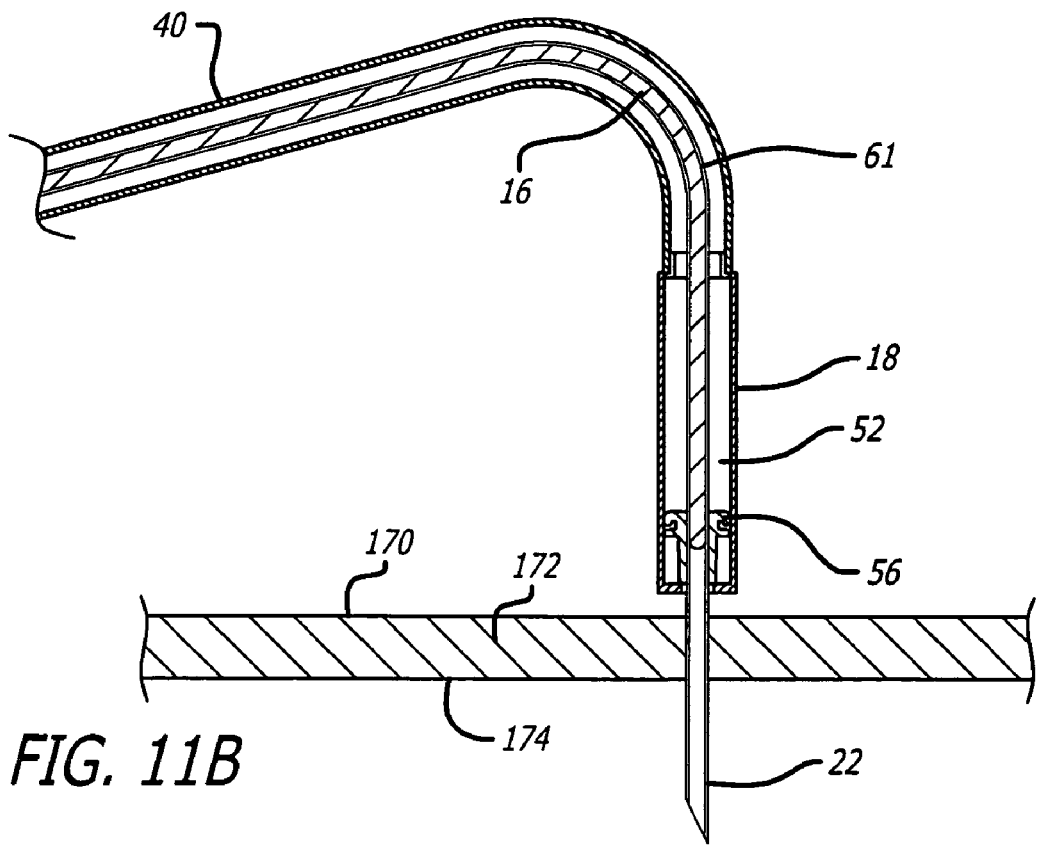
Figure 11C:
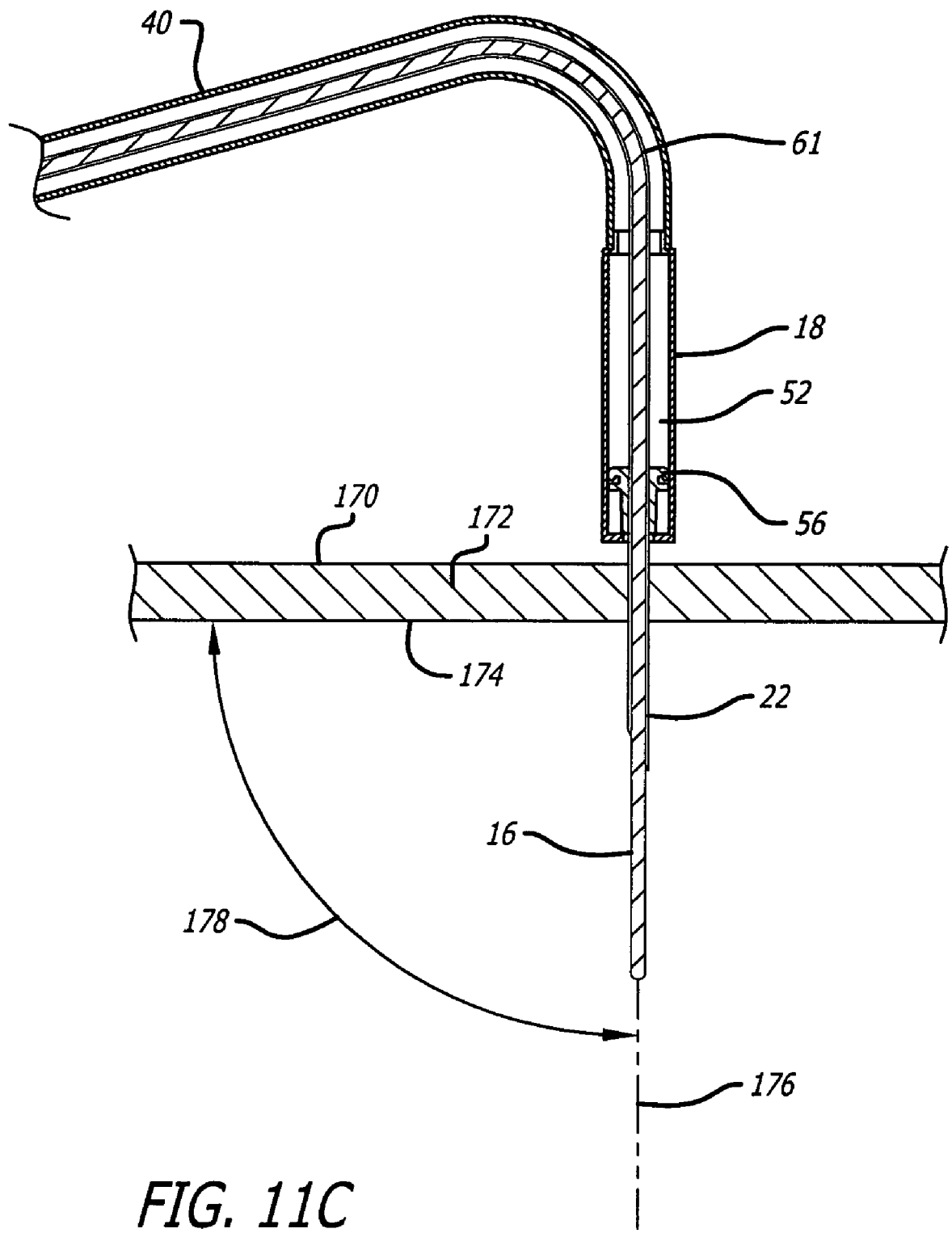

An embodiment of a method of use of access catheter 14 is illustrated in FIGS. 11A-11C. In FIG. 11A, the distal end of the housing 18 is positioned adjacent a first surface 170 of a tissue membrane 172. Upon achieving a desired positioning of the distal end of the housing 18, the tissue penetration member or needle 22 is actuated by actuation of the pressurized actuator 15. Thereafter, a pressurized fluid is ejected from the pressurized actuator in into the actuation lumen 68. Thereafter, pressurized fluid flows into the translation chamber 52 and forces the piston 56 and needle 22 forward distally such that the needle 22 exits the housing 18 contacts the tissue membrane 172 on the first surface 170, passes through the membrane 172 and exits a second surface 174 of the membrane 172, as shown in FIG. 11B. This process may be performed with the needle 22 at a high velocity upon contact with the first surface 170 or low velocity, however, a high velocity will reduce "tenting" of the tissue membrane which produces more accurate needle positioning in the membrane 172. Tenting may be undesirable for some procedures. In particular, when accessing the left atrium from the right atrium in a transseptal procedure, tenting of the fibro-muscular tissue of the intra-atrial septum may encroach on the left atrial cavity and reduce the distance between the distal tip of the needle 22 and other cardiac structures which may be vulnerable to perforation by the needle 22. In addition, resistive stored energy in the septal membrane due to tenting may release suddenly against the system 10 in an uncontrollable manner that may compromise the integrity of adjacent tissues that are not targeted for access. Finally, tenting may apply irregular non-axial loads to the needle 22 that result in deformation of the needle.

Once the tissue penetration member or needle 22 has penetrated the tissue wall 172 and is in communication with a second side 174 of the tissue membrane 172, the guidewire 16 can then be advanced through the needle lumen 78 and out of the access catheter 14 as shown in FIG. 11C. For some procedures or specific tissue membranes, such as intra-atrial septums, a high degree o f orthogonality may be desirable. The needle 22 has a longitudinal axis 176 that makes an angle indicated by arrow 178 shown in FIG. 11C. For some transseptal procedures, the angle 178 should be between about 70 degrees and 110 degrees. Once the guidewire 16 has been advanced from the needle lumen 78, the access catheter may be withdrawn from the position adjacent the tissue membrane 172. To accomplish this without moving the distal end of the guidewire or losing the guidewire's position across the tissue membrane, it may be desirable to use an exchange type guidewire which has a length at least slightly greater than two times that of the access catheter 14. Some guidewire embodiments can have a nominal outer diameter or transverse dimension of about 0.012 inches to about 0.040 inches, more specifically, about 0.025 inches to about 0.038 inches. Some guidewire embodiments may have a length of about 80 cm to about 300 cm. Suitable guidewires may include an Inoue type guidewire, as well as others.

Figure 12A:
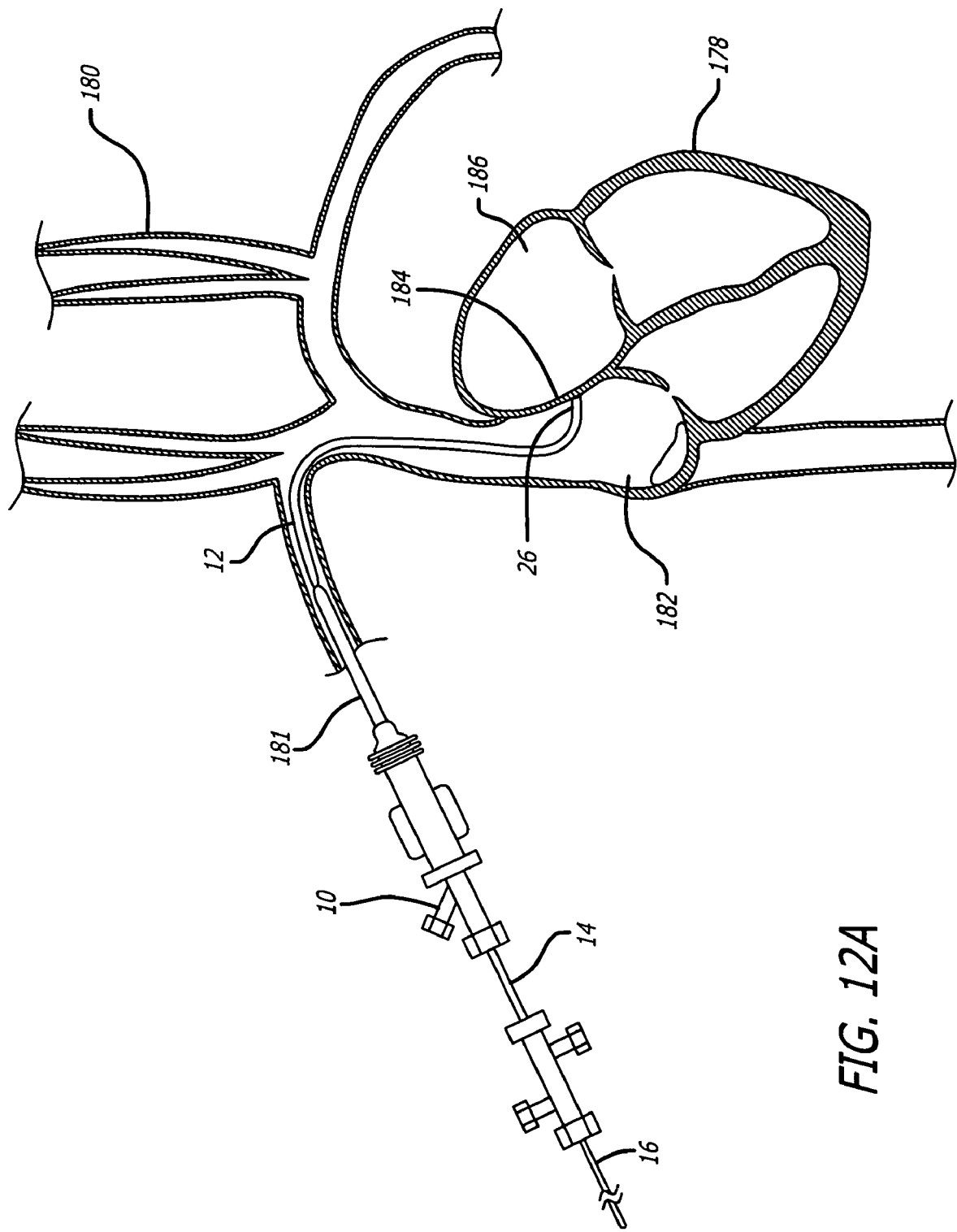
FIGS. 12A-12D illustrate an embodiment of a method sequence of transseptal access.
Figure 12B:
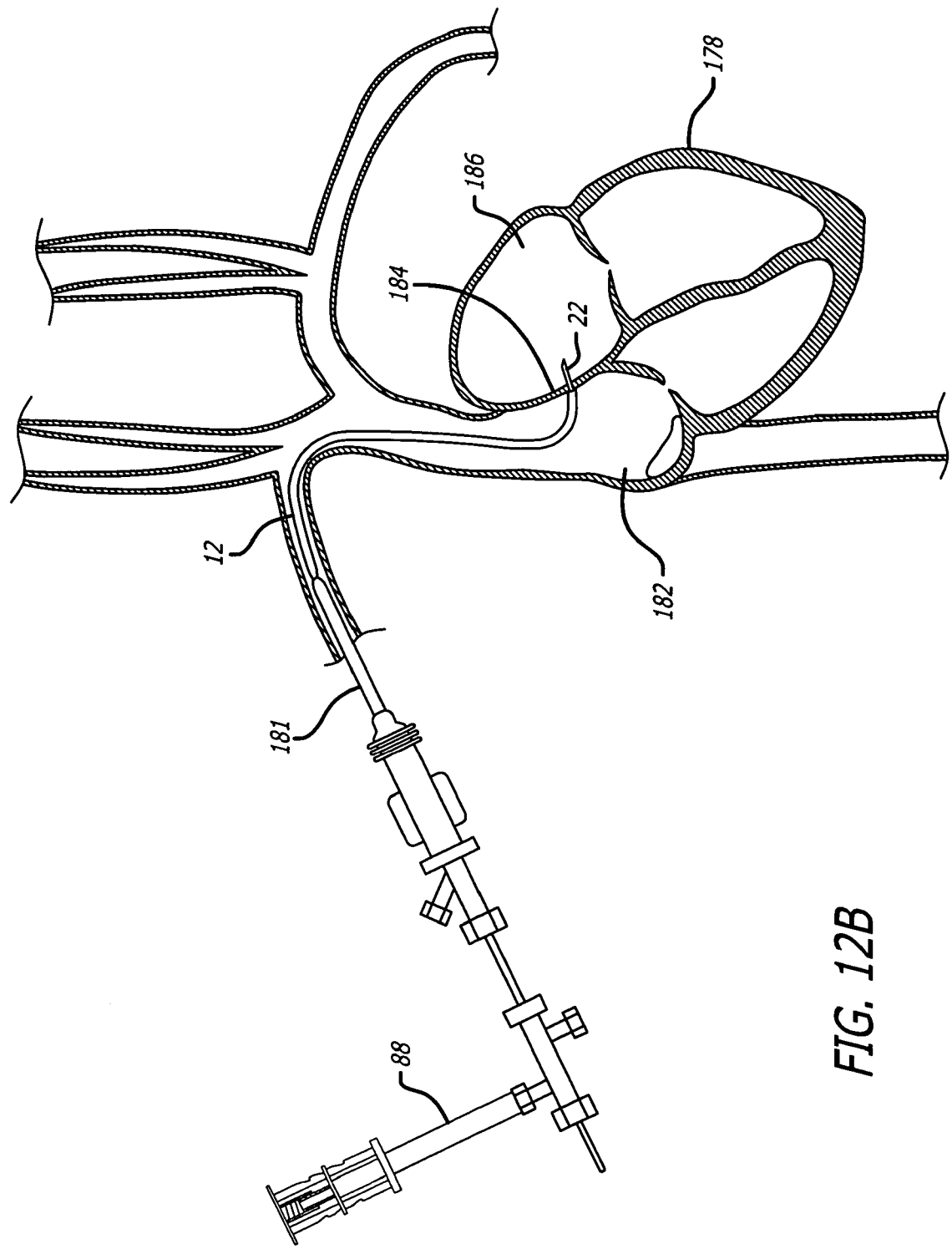
Figure 12C:
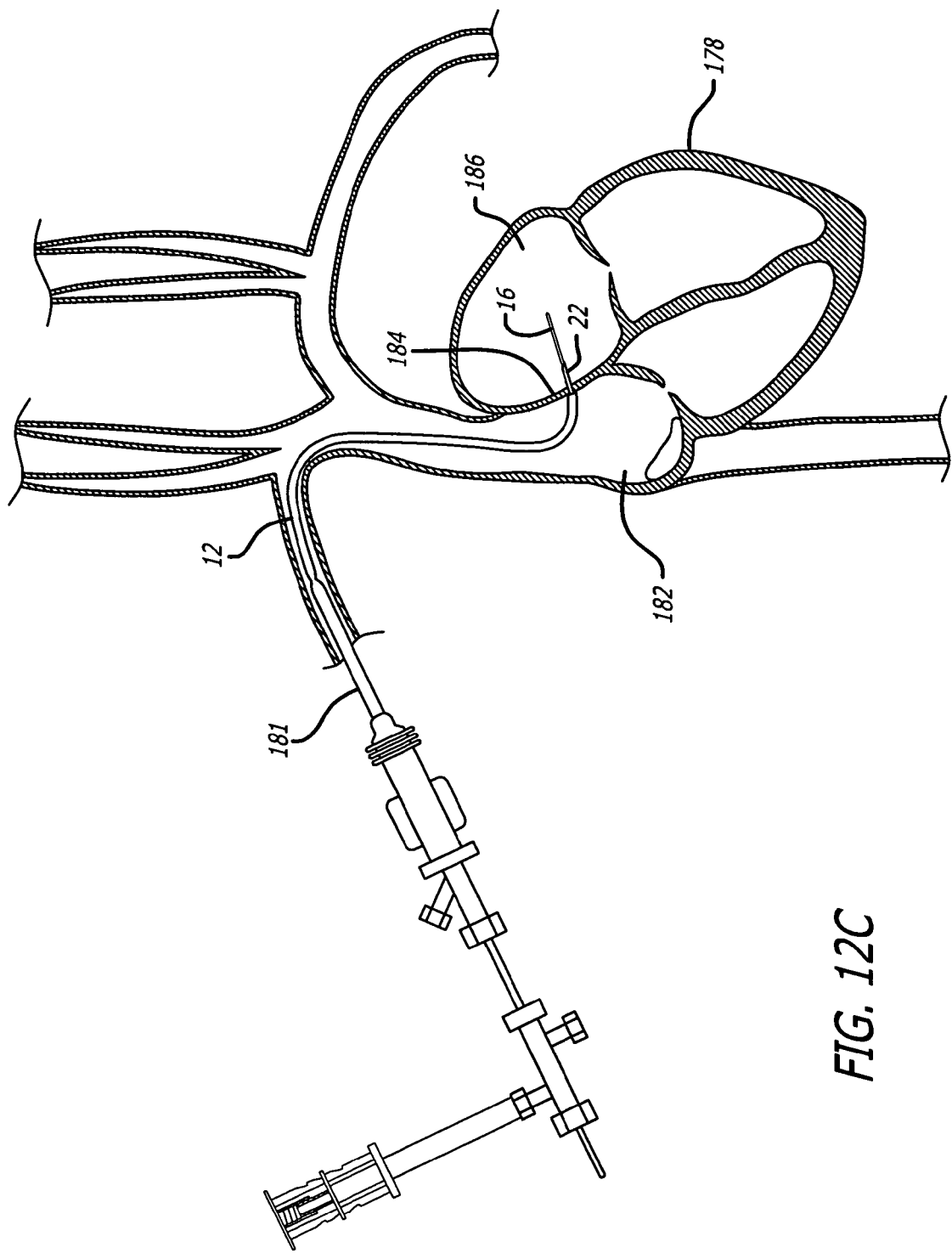
Figure 12D:
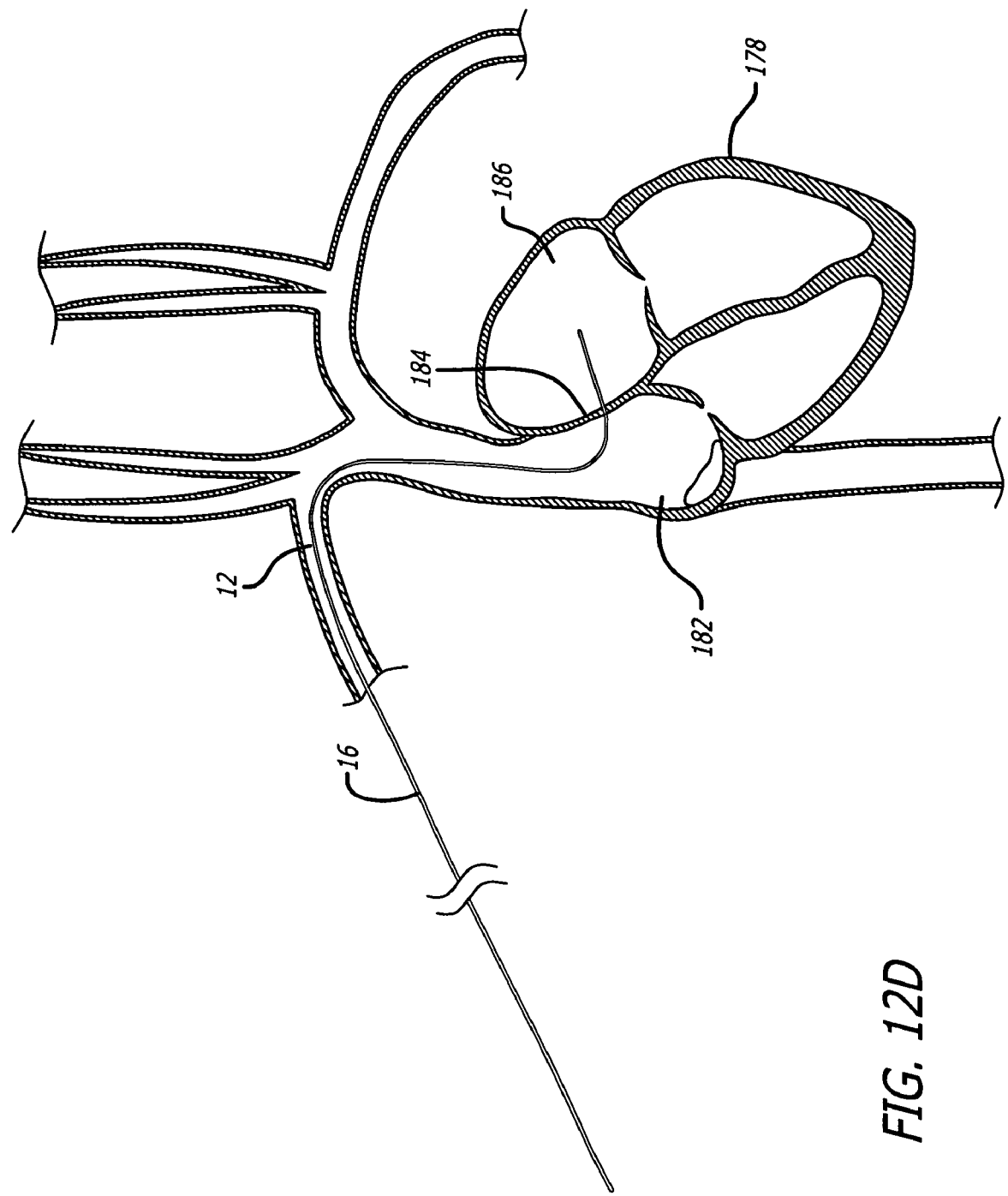

An embodiment of a method of use of the transseptal access system 10 in a patient's heart 178 is illustrated in FIGS. 12A-12D. In FIG. 12A, the distal end 26 of the guiding catheter 12 is advanced into the patient's vasculature 180 through a sheath 181, into the right atrium 182 and positioned with the distal end 26 of the guiding catheter 12 adjacent the intra-atrial septum 184 that separates the right atrium 182 from the left atrium 186. The distal end of the access catheter 14 is advanced through the guiding catheter 12 until the distal end of the access catheter 14 is disposed adjacent the septum 184. Thereafter, a pressurized tissue penetration actuator 88 is coupled to the proximal adapter 13 of the access catheter 14 and actuated such that the tissue penetration member or needle 22 is distally advanced at a high velocity through a first and second surface of the septum 184 and into the left atrium 186 of the heart 178, as shown in FIG. 12B. The guidewire 16 is then advanced through the guidewire lumen 78 of the needle 22 and into the left atrium 186 of the heart 178 while maintaining the needle 22 in a distally extended and actuated state as shown in FIG. 12C. Once the guidewire 16 is disposed across the septum 184 and into the left atrium 186, the guiding catheter 12 and access catheter 14 can then be removed from the patient or patient's heart 178 by proximally retracting the catheters 12 and 14 over the guidewire 16. Again, for this portion of the procedure, it may be desirable to have an exchange length guidewire that is more than two times the length of the access catheter 14. In addition, for any of the procedures discussed above, contrast media may be injected through the guidewire lumen 78 in order to verify the position of the needle 22 or for other imaging purposes. Injection of contrast media through lumen 78 may be performed with or without the guidewire 16 disposed within the lumen 78.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the invention. Accordingly, it is not intended that the invention be limited by the forgoing detailed description.

We claim:

1. A transseptal access system, comprising:
an elongate guiding catheter having a proximal end, a distal end and an inner lumen extending from the proximal end to the distal end thereof;
an access catheter which is configured to advance through the guiding catheter and which has
 an elongate catheter body section with an actuation lumen, a proximal end, a distal end and a distal section including a housing having a translation chamber in communication with the actuation lumen and bounded at least partially by an inner bore,
 a body section guidewire lumen separate from the actuation lumen and extending from the proximal end of the elongate catheter body section and disposed along the elongate catheter body section, and
 a hollow tissue penetration member having a sharpened tissue penetrating tip, a piston slidably sealed against the inner bore of the translation chamber of the housing and an outside surface of a distal section of a tubular element of the body section guidewire lumen and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and distal section of the tubular element from a retracted state with the sharpened distal tip disposed within the distal section of the catheter body section to a distally extended state with the sharpened distal tip extending distally beyond a distal end of the catheter body section; and
a tissue penetration actuator which includes a pressurized fluid actuator having a syringe actuated by a compressed spring, which is in fluid communication with the actuation lumen and which is configured to impinge fluid on the piston to impart high velocity translation in a distal direction on the tissue penetration member relative to the distal section of the elongate catheter body section.

2. A transseptal access system, comprising:
an elongate guiding catheter having a proximal end, a distal end and an inner lumen extending from the proximal end to the distal end thereof;
an access catheter which is configured to advance through the guiding catheter and which has
 an elongate catheter body section with an actuation lumen, a proximal end, a distal end and a distal section including a housing having a translation chamber in communication with the actuation lumen and bounded at least partially by an inner bore,
 a body section guidewire lumen separate from the actuation lumen and extending from the proximal end of the elongate catheter body section and disposed along the elongate catheter body section, and
 a hollow tissue penetration member having a sharpened tissue penetrating tip, a piston slidably sealed against the inner bore of the translation chamber of the housing and an outside surface of a distal section of a tubular element of the body section guidewire lumen and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and distal section of the tubular element from a retracted state with the sharpened distal tip disposed within the distal section of the catheter body section to a distally extended state with the sharpened distal tip extending distally beyond a distal end of the catheter body section; and
a tissue penetration actuator including a pressurized fluid actuator in fluid communication with the actuation lumen and configured to impinge fluid on the piston to impart high velocity translation in a distal direction on the tissue penetration member relative to the distal section of the elongate catheter body section.

3. A transseptal access system, comprising:
an elongate guiding catheter having a proximal end, a distal end and an inner lumen extending from the proximal end to the distal end thereof;
an access catheter which is configured to advance through the guiding catheter and which has
 an elongate catheter body section with an actuation lumen, a proximal end, a distal end and a distal section including a housing having a translation chamber in communication with the actuation lumen and bounded at least partially by an inner bore with a resilient rebound member disposed in the translation chamber proximally of a distal boundary of the translation chamber,
 a body section guidewire lumen separate from the actuation lumen and extending from the proximal end of the elongate catheter body section and disposed along the elongate catheter body section, and
 a hollow tissue penetration member having a sharpened tissue penetrating tip, a piston disposed proximally of the rebound member and slidably sealed against the inner bore of the translation chamber of the housing and an outside surface of a distal section of a tubular element of the body section guidewire lumen and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and distal section of the tubular element from a retracted state with the sharpened distal tip disposed within the distal section of the catheter body section to a distally extended state with the sharpened distal tip extending distally beyond a distal end of the catheter body section; and a tissue penetration actuator including a pressurized fluid actuator in fluid communication with the actuation lumen and configured to impinge fluid on the piston to impart high velocity translation in a distal direction on the tissue penetration member relative to the distal section of the elongate catheter body section.

4. The access system of claim 3 wherein the resilient rebound member extends from the piston to the distal boundary of the translation chamber and exerts a proximally directed force on the piston when the tissue penetration member is in a fully retracted state so as to fully retract the tissue penetration member when the tissue penetration actuator is not actuated.

5. A transseptal access system, comprising:

an elongate guiding catheter having a proximal end, a distal end and an inner lumen extending from the proximal end to the distal end thereof;

an access catheter which is configured to advance through the guiding catheter and which has an elongate catheter body section with a proximal end, a distal end and a distal section, a body section guidewire lumen extending from the proximal end of the elongate catheter body section and disposed along the elongate catheter body section, and a hollow tissue penetration member having a sharpened tissue penetrating tip, a piston slidably sealed against an outside surface of a distal section of a tubular element of the body section guidewire lumen and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and distal section of the tubular element from a retracted state with the sharpened distal tip disposed within the distal section of the catheter body section to a distally extended state with the sharpened distal tip extending distally beyond a distal end of the catheter body section;

a tissue penetration actuator configured to impart high velocity translation in a distal direction on the tissue penetration member relative to the distal section of the elongate catheter body section;

an interlock mechanism coupled to an interlock switch at the proximal end of the elongate catheter body section and configured to prevent distal translation of the tissue penetration member when in a locked state and allow distal translation of the tissue penetration member when in an unlocked state; and a distal contact member extending from the distal end of the access catheter and coupled to a contact trigger mechanism which is configured to prevent distal translation of the tissue penetration member when in a locked state and allow distal translation of the tissue penetration member when in an unlocked state when the interlock mechanism is also in an unlocked state whereby the contact trigger mechanism is unlocked upon contact with target tissue of the septum by the distal contact member.

6. A transseptal access system, comprising:

an elongate guiding catheter having a proximal end, a distal end and an inner lumen extending from the proximal end to the distal end thereof;

an access catheter which is configured to advance through the guiding catheter and which has an elongate catheter body section with a proximal end, a distal end and a distal section including a housing with a translation chamber, a body section guidewire lumen extending from the proximal end of the elongate catheter body section and disposed along the elongate catheter body section, and a hollow tissue penetration member having a sharpened tissue penetrating tip, a piston slidably sealed against an outside surface of a distal section of a tubular element of the body section guidewire lumen and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section from a retracted state with the sharpened distal tip disposed within the distal section of the catheter body section to a distally extended state with the sharpened distal tip extending distally beyond a distal end of the catheter body section;

a tissue penetration actuator including a spring disposed within the translation chamber and configured to exert a distally directed force on the tissue penetration member when released from a compressed state and impart high velocity translation in a distal direction on the tissue penetration member relative to the distal section of the elongate catheter body section.

7. The access system of claim 6 wherein the spring comprises a compressible spring in a compressed state disposed proximally of the tissue penetration member prior to actuation.

8. An access catheter, comprising:

an elongate catheter body section with a proximal end, a distal end, a distal section including a housing having a translation chamber bounded at least partially by an inner bore and an actuation lumen in communication with the translation chamber;

a body section guidewire lumen separate from the actuation lumen and extending from the proximal end of the elongate catheter body section and disposed along the elongate catheter body section;

a hollow tissue penetration member which has a piston slidably sealed against the inner bore of the translation chamber of the housing and an outside surface of a distal section of a tubular element of the body section guidewire lumen, a sharpened tissue penetrating tip and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and distal section of the tubular element from a retracted state with the sharpened distal tip disposed within the distal section of the catheter body section to a distally extended state with the sharpened distal tip extending distally beyond a distal end of the catheter body section; and a tissue penetration actuator which includes a pressurized fluid actuator having a syringe actuated by a compressed spring, which is in fluid communication with the actuation lumen of the elongate catheter body section and which is coupled to the tissue penetration member and configured to impinge fluid on the piston to impart high velocity translation in a distal direction on the tissue penetration member relative to the distal section of the elongate catheter body section.

9. An access catheter, comprising an elongate catheter body section with a proximal end, a distal end, a distal section including a housing having a translation chamber bounded at least partially by an inner bore and an actuation lumen in communication with the translation chamber;

a body section guidewire lumen extending from the proximal end of the elongate catheter body section and disposed along the elongate catheter body section;

a hollow tissue penetration member which has a piston slidably sealed against the inner bore of the translation chamber of the housing and an outside surface of a distal section of a tubular element of the body section guidewire lumen, a sharpened tissue penetrating tip and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and distal section of the tubular element from a retracted state with the sharpened distal tip disposed within the distal section of the catheter body section to a distally extended state with the sharpened distal tip extending distally beyond a distal end of the catheter body section; and a tissue penetration actuator including a pressurized fluid actuator in fluid communication with the actuation lumen of the elongate catheter body section coupled to the tissue penetration member and configured to impinge fluid on the piston to impart high velocity translation in a distal direction on the tissue penetration member relative to the distal section of the elongate catheter body section.

10. An access catheter, comprising:

an elongate catheter body section with a proximal end, a distal end, a distal section including a housing having a translation chamber bounded at least partially by an inner bore and an actuation lumen in communication with the translation chamber;

a body section guidewire lumen separate from the actuation lumen and extending from the proximal end of the elongate catheter body section and disposed along the elongate catheter body section;

a hollow tissue penetration member which has a piston slidably sealed against the inner bore of the translation chamber of the housing and an outside surface of a distal section of a tubular element of the body section guidewire lumen, a sharpened tissue penetrating tip and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and a distal section of the tubular element from a retracted state with the sharpened distal tip disposed within the distal section of the catheter body section to a distally extended state with the sharpened distal tip extending distally beyond a distal end of the catheter body section;

a resilient rebound member disposed in the translation chamber between a distal end of the piston and a distal boundary of the translation chamber; and a tissue penetration actuator which includes a pressurized fluid actuator in fluid communication with the actuation lumen of the elongate catheter body section, which is coupled to the tissue penetration member and which is configured to impinge fluid on the piston to impart high velocity translation in a distal direction on the tissue penetration member relative to the distal section of the elongate catheter body section.

11. The access catheter of claim 10 wherein the resilient rebound member extends from the piston to the distal boundary of the translation chamber and exerts a proximally directed force on the piston when the tissue penetration member is in a fully retracted state so as to fully retract the tissue penetration member when the tissue penetration actuator is not actuated.

12. An access catheter, comprising:

an elongate catheter body section with a proximal end, a distal end and a distal section;

a body section guidewire lumen extending from the proximal end of the elongate catheter body section and disposed along the elongate catheter body section;

a hollow tissue penetration member which has a sharpened tissue penetrating tip, a piston slidably sealed against an outside surface of a distal section of a tubular element the body section guidewire lumen and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section and a distal section of the tubular element from a retracted state with the sharpened distal tip disposed within the distal section of the catheter body section to a distally extended state with the sharpened distal tip extending distally beyond a distal end of the catheter body section;

a tissue penetration actuator coupled to the tissue penetration member and configured to impart high velocity translation in a distal direction on the tissue penetration member relative to the distal section of the elongate catheter body section;

an interlock mechanism coupled to an interlock switch at the proximal end of the elongate catheter body section and configured to prevent distal translation of the tissue penetration member when in a locked state and allow distal translation of the tissue penetration member when in an unlocked state; and a distal contact member extending from the distal end of the access catheter and coupled to a contact trigger mechanism which is configured to prevent distal translation of the tissue penetration member when in a locked state and allow distal translation of the tissue penetration member when in an unlocked state when the interlock mechanism is also in an unlocked state whereby the contact trigger mechanism is unlocked upon contact with target tissue of the septum by the distal contact member.

13. An access catheter, comprising:

an elongate catheter body section with a proximal end, a distal end and a distal section including a housing with a translation chamber;

a body section guidewire lumen extending from the proximal end of the elongate catheter body section and disposed along the elongate catheter body section;

a hollow tissue penetration member which has a sharpened tissue penetrating tip, a piston slidably sealed against an outside surface of a distal section of a tubular element of the body section guidewire lumen and a guidewire lumen in fluid communication and aligned with the body section guidewire lumen to allow a guidewire to be advanced from the body section guidewire lumen into the tissue penetration member guidewire lumen, the tissue penetration member being disposed at the distal section of the elongate catheter body section and axially displaceable in a distal direction with respect to the distal section of the elongate catheter body section from a retracted state with the sharpened distal tip disposed within the distal section of the catheter body section to a distally extended state with the sharpened distal tip extending distally beyond a distal end of the catheter body section; and a tissue penetration actuator which includes a spring disposed within the translation chamber and configured to exert a distally directed force on the tissue penetration member when released from a compressed state and which is coupled to the tissue penetration member and configured to impart high velocity translation in a distal direction on the tissue penetration member relative to the distal section of the elongate catheter body section.

14. The access catheter of claim 13 wherein the spring comprises a compressible spring in a compressed state disposed proximally of the tissue penetration member prior to actuation.

* * * * *